United States Patent [19]

Welstead, Jr.

[11] 3,978,129

[45] Aug. 31, 1976

[54] ALKENYL- AND ALKANYLAMINES

[75] Inventor: William John Welstead, Jr., Richmond, Va.

[73] Assignee: A. H. Robins Company, Incorporated, Richmond, Va.

[22] Filed: Jan. 28, 1972

[21] Appl. No.: 221,825

[52] U.S. Cl. .................. 260/570.5 R; 260/293.72; 260/501.1; 260/562 R; 260/563 R; 260/570.6; 260/590 C; 424/267; 424/316; 424/330

[51] Int. Cl.² .................. C07C 87/28; C07C 87/29

[58] Field of Search .................. 260/520.5 R, 501.1

[56] References Cited

UNITED STATES PATENTS 3,573,304  3/1971  Eberle et al. ............... 260/570.8 X

OTHER PUBLICATIONS

Vartanyan et al. "Chemical Abstracts", vol. 70, pp. 291, Abstract 96277O (1969).

Hoffsommer et al., "Journal of Organic Chemistry", vol. 27, pp. 4134–4137 (1962).

Primary Examiner—Robert V. Hines

[57] ABSTRACT

Novel alkenyl- and alkanylamines having the formula:

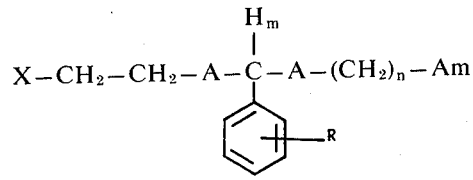

wherein Am is lower-alkylamino, di-lower-alkylamino and piperidino; A is methylene and methylidyne; R is hydrogen, lower-alkyl, lower-alkoxy, halogen and trifluoromethyl; $m$ is zero and one; $n$ is one and two; X is halogen and the pharmaceutically acceptable acid addition salts thereof. The alkenylamines are prepared by contacting 1-cyclopropyl-1-phenyl-ω-amino-1-alkanols with strong mineral acids. The alkanylamines are prepared by hydrogenation of the alkenylamines. Some of the compounds exhibit potent antagonism to the depressant effects of tetrabenazine.

9 Claims, No Drawings

ALKENYL- AND ALKANYLAMINES

The present invention relates to novel ω-haloalkenylamines and ω-haloalkanylamines and is more particularly concerned with 6-halo-3-phenyl-2-(and 3-)hexenylamines, 7-halo-4-phenyl-3-(and 4-)heptenylamines and the corresponding alkanes, compositions thereof and methods of making and using the same.

The invention is especially concerned with novel compounds having the formula:

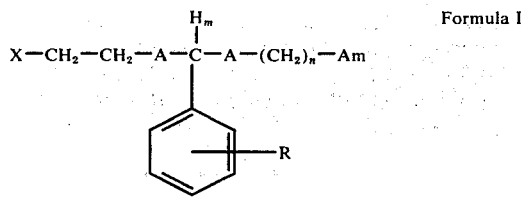

Formula I wherein;
Am is lower-alkylamino, di-lower-alkylamino and piperidino,
A is methylene and methylidyne,
R is hydrogen, lower-alkyl, lower-alkoxy, halogen and trifluoromethyl,
m is zero and one,
n is one and two,
X is halogen, and
the pharmaceutically acceptable acid addition salts thereof.

The novel concept of the present invention resides in the opening of the cyclopropyl ring and dehydration of the 1-cyclopropyl-3-(and 4-) amino-1-phenyl-1-alkanol starting materials by contacting them with strong mineral acids to produce the novel 6-halo-3-phenyl-2-(and 3-)hexenylamines and 7-halo-4-phenyl-3-(and 4-)heptenylamines of the invention. Catalytic hydrogenation of the alkenylamines furnishes the corresponding alkanylamines.

The compounds represented by Formula I were observed to be especially effective in blocking the depressant effects of tetrabenazine and can therefore be considered to be major tranquilizers.

The compounds were administered to mice intraperitoneally and the effectiveness of the compounds in blocking the depressant effects which are induced in mice by intravenous administration of 2-oxo-3-isobutyl-9,10-di-methoxy-1,2,3,4,6,7-hexahydro-11-bh-benzo[a]quinolizine (tetrabenazine was determined. The procedure used was a modification of that given by Englehardt, E. L. et al, J. Med. Chem. 11 (2) : 325(1968) wherein tetrabenazine dosage is increased over the Englehardt procedure. The $ED_{50}$ of the compounds tested in blocking the depressant activity of tetrabenazine are given in Table I.

TABLE I

| Example NO. | $ED_{50}$ mg/kg. I.P. |
|---|---|
| 1 | 2.5 |
| 2 | 0.5 |
| 3 | 1.9 |
| 4 | 20.0 |
| 5 | 10.0 |
| 6 | 28.5 |
| 7 | 15.5 |
| 8 | 3.6 |

It is, accordingly, an object of the present invention to provide new and useful phenyl-ω-haloalkenylamines and phenyl-ω-haloalkanylamines, compositions thereof and methods of making and using the same. Other objects of the invention will be apparent to one skilled in the art and still other objects will become apparent hereinafter.

In the definition of symbols in foregoing Formula I and where they appear elsewhere throughout the specification, the terms used herein have the following significance.

"Lower-alkyl" as used herein includes straight and branched chain radicals of up to eight carbon atoms inclusive and is exemplified by such groups as methyl, ethyl, propyl, isopropyl, butyl, isobutyl, amyl, isoamyl, hexyl, heptyl, octyl and the like. Lower-alkoxy has the formula -O-lower-alkyl.

When halogen is referred to herein, chlorine and bromine are preferred.

Method of Preparation

The preparation of the novel 6-halo-3-phenyl-2-(and 3-) hexenylamines (I), 7-halo-4-phenyl-3-(and 4-)heptenylamines (I), 6-halo-3-phenylhexylamines (I), and 7-halo-4-phenylheptylamines (I) may be accomplished by mixing and reacting 1-cyclopropyl-1-phenyl-ω-amino-1-alkanols (II) with concentrated halogen acids (III) and hydrogenation of the alkenyl compounds obtained thereby to the alkanyl compounds (I). The reaction sequence is illustrated by the following:

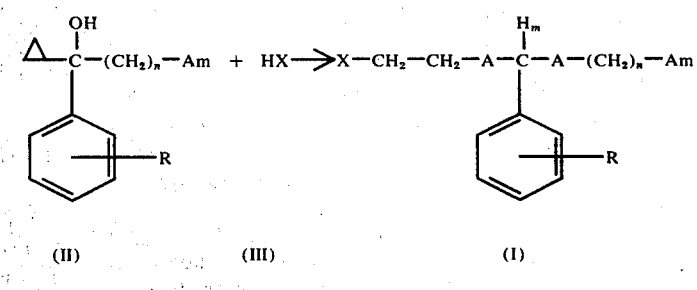

wherein Am, A, R and X have the values hereinabove assigned and m is zero, and $$X-CH_2-CH_2-A-\underset{\underset{\displaystyle\phantom{X}}{\phantom{C}}}{\overset{\overset{\displaystyle H_m}{|}}{C}}-A-(CH_2)_n-Am \xrightarrow{H_2} X-CH_2-CH_2-A-\underset{\underset{\displaystyle\phantom{X}}{\phantom{C}}}{\overset{\overset{\displaystyle H_m}{|}}{C}}-A-(CH_2)_n-Am$$

(with phenyl-R substituent on central C in both structures)

(I)     (I)

wherein Am, A, R and X have the values hereinabove assigned and $m$ is zero and one respectively.

The method of preparing the starting materials used in preparing the novel compounds of the present invention are described hereinafter in Preparations I-X.

Preparation I

1-Cyclopropyl-3-dimethylamino-1-phenyl-1-propanol.

An ether solution of phenyl lithium was prepared by reacting 31.4 g. (0.2 mole) of bromobenzene in 30 ml. of ether with 2.8 g. (0.4 mole) of lithium in 30 ml. of ether. The mixture was allowed to stir under nitrogen overnight. The mixture was cooled to −30°C. and treated slowly with 24.8 g. (0.175 mole) of cyclopropyl-2-dimethylaminoethyl ketone, keeping the temperature below −20°C. After most of the ketone had been added, a precipitate formed. To facilitate stirring, an additional 50 ml. of ether was added. The mixture was stirred and allowed to warm to room temperature over a three-hour period, then poured onto ice. The ether layer was separated, dried over magnesium sulfate and evaporated under reduced pressure. The residue was distilled at 70°–72°C./0.01 mm; yield 23.5 g. (61%) of the free base. The nuclear magnetic resonance spectrum of the oil was consistent with the cyclopropyl structure. Vapor phase chromatography gave a single peak.

Preparation II

1-Cyclopropyl-3-dimethylamino-1-phenyl-1-propanol Hydrochloride.

Seven grams of the oil from Preparation I was converted to the hydrochloride salt by ethereal hydrogen chloride. Recrystallization from isopropanol-isopropyl ether gave 2.6 g. of the pure hydrochloride salt which melted at 157°–159°C.

Analysis: Calculated for $C_{14}H_{22}ClNO$: C, 65.73; H,8.67; N,5.48;
Found: C,65.44; H,8.46; N,5.59

Preparation III

1-Cyclopropyl-4-dimethylamino-1-phenyl-1-butanol.

A tetrahydrofuran solution of 3-dimethylaminopropylmagnesium chloride was prepared from 100 g. (0.66 mole) of 3-dimethylaminopropyl chloride and 15.5 g. (0.66 mole) of magnesium metal in 200 ml. of tetrahydrofuran. The solution was treated dropwise with 46 g. (0.32 mole) of cyclopropyl phenyl ketone in 100 ml. of tetrahydrofuran. After the addition the mixture was refluxed for one hour, cooled and treated with 300 ml. of water containing 33.7 g. (0.63 mole) of ammonium chloride. The mixture was filtered through glass wool with the aid of celite and the tetrahydrofuran layer was separated from the aqueous layer. The aqueous layer was washed twice with two 10 ml. portions of ether and the ether wash was combined with the tetrahydrofuran layer which was then dried over magnesium sulfate and concentrated to an oil. The oil was distilled at 90°–96°C./0.14 mm. The yield of the free base was 61 g. (83%).

Preparation IV

1-Cyclopropyl-4-dimethylamino-1-phenyl-1-butanol Hydrochloride.

1-Cyclopropyl-4-dimethylamino-1-phenyl-1-butanol was converted to the hydrochloride salt which after recrystallization from isopropanol-isopropyl ether melted at 153°–155°C.

Analysis: Calculated for $C_{15}H_{24}ClNO$: C,66.77; H,8.97; N,5.19; Found: C,66.75; H,8.82; N,5.19

PREPARATION V

1-Cyclopropyl-3-dimethylamino-1-(4-methoxyphenyl)-1-propanol.

The Grignard reagent prepared from 86 g. (0.46 mole) of 4-bromoanisole and 11.2 g. (0.46 mole) of magnesium metal in 200 ml. of dry ether was cooled to −20°C. and treated dropwise with 30 g. (0.23 mole) of cyclopropyl 2-dimethylaminoethyl ketone in 100 ml. of dry ether. After addition the mixture was allowed to warm to room temperature, then hydrolyzed with water and worked up as described in Preparation I. The oily product was distilled at 110°–115°C./0.1 mm.; the yield of free base was 16 g. (28%).

Preparation VI

1-Cyclopropyl-3-dimethylamino-1-(4-methoxyphenyl)-1-propanol Hydrobromide.

The free base was dissolved in ether and treated with hydrogen bromide gas and the salt precipitated. It melted at 175°–177°C. after recrystallization from isopropanol-isopropyl ether.

Analysis: Calculated for $C_{15}H_{24}BrNO_2$: C,54.59; H,7.33; N,4.24; Found: C,54.76; H,7.38; N,4.26

Preparation VIII

1-Cyclopropyl-3-dimethylamino-1-(3-trifluoromethylphenyl)-1-propanol.

The Grignard reagent prepared from 64 g. (0.28 mole) of 3-bromobenzotrifluoride and 7 g. (0.28 mole) of magnesium in ether was cooled to −30°C., and 20 g. (0.14 mole) of cyclopropyl 2-dimethylaminoethyl ketone in 100 ml. of ether was added dropwise to the stirred mixture at a rate sufficient to maintain a temperature below −20°C. The mixture was allowed to warm to room temperature and then worked up as described in Preparation I. Distillation of the crude product gave 10 g. of oil which distilled at 78°–83°C./0.12 mm.

Preparation VIII

1-Cyclopropyl-3-dimethylamino-1-(3-trifluoromethylphenyl)-1-propanol Hydrochloride.

1-Cyclopropyl-3-dimethylamino-1-(3-trifluoromethylphenyl)-1-propanol was converted to the hydrochloride salt which melted at 170°–172°C. after recrystallization from isopropanol-isopropyl ether.

Analysis: Calculated for $C_{15}H_{21}ClF_3NO$: C,55.64; H,6.54; N,4.33; Found: C,55.99; H,6.52; N,4.42

Preparation IX

1-Cyclopropyl-3-piperidinyl-1-(3-trifluoromethylphenyl)-1-propanol Hydrochloride.

The Grignard reagent prepared from 14.5 g. (0.6 mole) of magnesium and 136 g. (0.6 mole) of m-bromobenzotrifluoride in 800 ml. of dry ether was cooled to −30°C. and treated with 53.5 g. (0.296 mole) of crude cyclopropyl 2-piperidinylethyl ketone in 200 ml. of ether at a rate that the temperature was maintained below −20°C. After addition, the mixture was stirred and allowed to warm to room temperature over a one-hour period. The reaction mixture was treated with 32 g. of ammonium chloride in 170 ml. of water and the ether layer was separated. The remainder of the reaction mixture was filtered and the resulting solid precipitate was extracted with 200 ml. portions of ether. The combined ether extracts were dried over magnesium sulfate and concentrated to an oil. The oil was distilled under reduced pressure and the distillate was converted to the hydrochloride salt. Recrystallization from acetone-ethanol mixture gave 3.6 g. (17%) of pure product which melted at 193°–194°C. after drying.

Analysis: Calculated for $C_{18}H_{25}ClF_3NO$: C,59.42; H,6.93; N,3.85; Found: C,59.46; H,6.96; N,3.73

Preparation X

1-Cyclopropyl-3-methylamino-1-(3-trifluoromethylphenyl)-1-propanol.

A mixture of 5 g. (0.016 mole) of 1-cyclopropyl-3-(N-methylacetamido)-1-(3-trifluoromethylphenyl)-1-propanol, 2.9 g. (0.024 mole) of potassium tertiary butoxide and 25 ml. of dimethyl sulfoxide was warmed on a steam bath for 45 minutes. The mixture was cooled, poured into ice water and extracted with benzene. The benzene extract was dried over magnesium sulfate and concentrated to an oil which was distilled at 108°C./0.15 mm. The yield was 2.6 g. (59%).

Analysis: Calculated for $C_{14}H_{18}F_3NO$: C,61.53; H,6.63; N,5.13;

Found: C,61.73; H,6.59; N,4.95

The following examples are presented to illustrate the preparation of compounds of the present invention and they should not be construed as limiting it in spirit or in scope.

EXAMPLE 1

6-Chloro-N,N-dimethyl-3-phenyl-3-hexenylamine Hydrochloride.

The acidic filtrate remaining after the separation of 1-cyclopropyl-3-dimethylamino-1-phenyl-1-propanol hydrochloride in Preparation II was cooled and a second crop of crystals was isolated which was recrystallized from ethyl-acetate. The yield of crystals melting at 148°–150°C. was 1.6 g. The nuclear magnetic resonance spectrum indicated the structure to be 6-chloro-N,N-dimethyl-3-phenyl-3-hexenylamine hydrochloride.

Analysis: Calculated for $C_{14}H_{21}Cl_2N$: C,61.31; H,7.72; N,5.11; Found: C,61.38; H,7.60; N,4.70

Example 2

6-Bromo-N,N-dimethyl-3-phenyl-2-hexenylamine Hydrobromide.

A solution of 30 g. (0.14 mole) of 1-cyclopropyl-3-dimethylamino-1-phenyl-1-propanol in 200 ml. of 48% hydrogen bromide was heated at 100°C. for several minutes and then concentrated on a rotating evaporator. The residual oil was dissolved in isopropanol and treated with ether to give an amorphous solid. Recrystallization of the solid from ethyl acetate gave a nearly pure isomer which after additional recrystallization from isopropylmethyl ketone melted at 128°–130°C. The yield was 2.6 g. (5.2%). The nuclear magnetic resonance spectrum showed the double bond to be in position 2 of the hexenylamine.

Analysis: Calculated for $C_{14}H_{21}Br_2N$: C,46.30; H,5.83; N,3.86; Found: C,46.42; H,5.78; N,3.87

Example 3

6-Bromo-N,N-dimethyl-N,N-dimethyl-3-hexenylamine Hydrobromide.

From the filtrate of Example 2, a second isomer was obtained which, after several recrystallizations from ethyl acetate, melted at 143°–145°C. The yield of this isomer was 1.2 g. (2.3%). The nuclear magnetic resonance spectrum of this isomer showed the double bond to be in position 3 of the hexenylamine.

Analysis: Calculated for $C_{14}H_{21}Br_2N$: C, 46.30; H, 5.83; N, 3.86; Found: C, 46.37; H, 5.80; N, 3.89

EXAMPLE 4

7-Chloro-N,N-dimethyl-4-phenyl-4-heptenylamine Oxalate.

A mixture of 10 g. (0.043 mole) of 1-cyclopropyl-4-dimethylamino-1-phenyl-1-butanol from Preparation III in 75 ml. of 6N hydrochloric acid was warmed on a steam bath until all the starting material dissolved. The mixture was immediately cooled in ice and made basic with 3N sodium hydroxide. The mixture was extracted with ether and the extract dried over magnesium sulfate. A solution of oxalic acid in isopropanol was added to the ether extract and the resulting oxalate salt was recrystallized several times from isopropanol. The yield of the oxalate salt melting at 137°–139°C. was 7.5 g. (52%).

Analysis: Calculated for $C_{17}H_{24}ClNO_4$: C, 59.73; H, 7.08; N, 4.10; Found: C, 59.60; H, 7.14; N, 4.04

EXAMPLE 5

7-Chloro-N,N-dimethyl-4-phenyl-3-heptenylamine Oxalate.

A mixture of 10 g. (0.043 mole) of 1-cyclopropyl-4-dimethylamino-1-phenyl-1-butanol from Preparation III in 75 ml. of 6N hydrochloric acid was warmed on a steam bath until all the starting material dissolved and for an additional five minutes. The mixture was immediately cooled in ice and made basic with 3N sodium hydroxide. The product was extracted into ether and the extract then dried over magnesium sulfate. A solution of oxalic acid in isopropanol was added to the ether extract and the resulting oxalate salt was recrystallized several times from isopropanol. The yield of the oxalate salt melting at 151°–155°C. was 2 g. (14%).

Analysis: Calculated for $C_{17}H_{24}ClNO_4$: C, 59.73; H, 7.08; N, 4.10; Found: C, 59.90; H, 7.11; N, 4.07

EXAMPLE 6

6-Chloro-N,N-dimethyl-3-(4-methoxyphenyl)-3-hexenylamine Hydrochloride

1-Cyclopropyl-3-di-methylamino-1-(4-methoxyphenyl)-1-propanol was dissolved in ether and ethereal hydrogen chloride was added to the ether solution. The ether insoluble hydrochloride salt was separated by filtration and recrystallized from isopropanol.

Analysis: Calculated for $C_{15}H_{23}Cl_2NO$: C, 59.21; H, 7.62; N, 4.60; Found: C, 59.57; H, 7.62; N, 4.62

EXAMPLE 7

6-Chloro-N,N-dimethyl-3-(3-trifluoromethylphenyl)-3-hexenylamine Oxalate.

A mixture of 6.8 g. (0.02 mole) of 1-cyclopropyl-3-dimethylamino-1-(3-trifluoromethylphenyl)-1-propanol in 60 ml. of 6N hydrochloric acid was warmed on a steam bath until all the solid had dissolved. The solution was immediately cooled with ice and made basic with 3N sodium hydroxide. The product was extracted into ether and the extract dried over magnesium sulfate. A solution of oxalic acid in isopropanol was added to the ether extract, the ether insoluble oxalate salt was separated and recrystallized several times from isopropanol. The 3.5 g. (47%) of oxalate salt melted at 151°–153°C.

Analysis: Calculated for $C_{17}H_{21}ClF_3NO_4$: C, 51.58; H, 5.35; N, 3.54; Found: C, 51.99; H, 5.46; N, 3.50

EXAMPLE 8

6-Chloro-N,N-dimethyl-3-phenylhexylamine Hydrochloride

A solution of 10 g. (0.037 mole) of 6-chloro-N,N-dimethyl-3-phenyl-3-hexenylamine hydrochloride in 150 ml. of 95% ethanol was hydrogenated using palladium on carbon catalyst. Hydrogenation was complete after 15 minutes at room temperature. The catalyst was removed by filtration and the filtrate was evaporated to a solid. Recrystallization of the solid from isobutyl methyl ketone gave 7 g. (70%) of a hygroscopic solid.

Analysis: Calculated for $C_{14}H_{23}Cl_2N$: C, 60.87; H, 8.30; N, 5.07; Found: C, 60.74; H, 8.16; N, 5.27

EXAMPLE 9

6-Bromo-1-piperidinyl-3-(3-trifluoromethylphenyl)-3-hexene Hydrobromide.

Following the procedure of Example 2, 1-cyclopropyl-3-piperidinyl-1-(3-trifluoromethylphenyl)-1-propanol was converted to 6-bromo-1-piperidinyl-3-(3-trifluoromethylphenyl)-3-hexene hydrobromide.

EXAMPLE 10

When in the procedure of Example 7, 1-cyclopropyl-3-dimethylamino-1-(3-trifluoromethylphenyl)-1-propanol is replaced by equal molar amounts of 1-cyclopropyl-3-methylamino-1-(3-trifluoromethyphenyl)-1-propanol, 1-cyclopropyl-3-methylamino-1-phenylpropanol, and 1-cyclopropyl-3-methylamino-1-phenylbutanol, there are obtained 6-chloro-N-methyl-3-(3-trifluoromethylphenyl)-3-hexenylamine oxalate, 6-chloro-N-methyl-3-(3-trifluoromethylphenyl)-3-hexenylamine oxalate, and 7-chloro-N-methyl-4-phenyl-3-heptenylamine oxalate.

EXAMPLE 11

When in the procedure of Example 8, 6-chloro-N,N-dimethyl-3-phenyl-3-hexenylamine hydrochloride is replaced by equal molar amounts of 7-chloro-N,N-dimethyl-4-phenyl-4-heptenylamine hydrochloride, 6-chloro-N,N-dimethyl-3-(4-methoxyphenyl)-3-hexenylamine hydrochloride, and 6-chloro-N,N-dimethyl-3-(3-trifluoromethylphenyl)-3-hexenylamine hydrochloride, there are obtained 7-chloro-N,N-dimethyl-3-phenylheptylamine hydrochloride, 6-chloro-N,N-dimethyl-(4-methoxyphenyl)-hexylamine hydrochloride, and 6-chloro-N,N-dimethyl-(3-trifluoromethylphenyl)-hexylamine hydrochloride.

Effective quantities of any of the foregoing pharmacologically active compounds of Formula I may be administered together with a pharmaceutically acceptable carrier to a living animal body for therapeutic purposes according to usual modes of administration and in usual forms such as orally, in solutions, emulsions, suspensions, pills, tablets and capsules, or intramuscularly or parenterally in the form of sterile solutions.

What is claimed is:

1. A compound selected from alkenyl and alkanylamines having the formula:

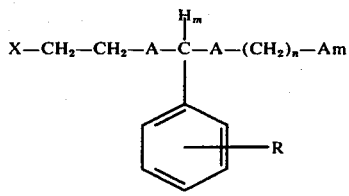

wherein:
Am is selected from lower-alkylamino and di-lower-alkylamino.
A is selected from methylene and methylidyne,
R is selected from hydrogen, lower-alkyl, lower-alkoxy, halogen and trifluoromethyl,
$m$ is selected from zero and one,
$n$ is one and two,
X is halogen, and the pharmaceutically acceptable acid addition salts thereof.

2. A compound of claim 1 which is 6-chloro-N,N-dimethyl-3-phenyl-3-hexenylamine.

3. A compound of claim 1 which is 6-bromo-N,N-dimethyl-3-phenyl-2-hexenylamine.

4. A compound of claim 1 which is 6-bromo-N,N-dimethyl-3-phenyl-3-hexenylamine.

5. A compound of claim 1 which is 7-chloro-N,N-dimethyl-4-phenyl-4-heptenylamine.

6. A compound of claim 1 which is 7-chloro-N,N-dimethyl-4-phenyl-3-heptenylamine.

7. A compound of claim 1 which is 6-chloro-N,N-dimethyl-3-(4-methoxyphenyl)-3-hexenylamine.

8. A compound of claim 1 which is 6-chloro-N,N-dimethyl-3-(3-trifluoromethylphenyl)-3-hexenylamine.

9. A compound of claim 1 which is 6-chloro-N,N-dimethyl-3-phenylhexylamine.

* * * * *